(12) United States Patent
Igarashi et al.

(10) Patent No.: US 6,815,215 B2
(45) Date of Patent: Nov. 9, 2004

(54) METHOD OF RECOVERING A PLURALITY OF NUCLEIC ACIDS BY AN IDENTICAL STATIONARY PHASE AND AN APPARATUS THEREOF

(75) Inventors: Yoshiaki Igarashi, Mito (JP); Toshinari Sakurai, Hitachinaka (JP); Toshiaki Yokobayashi, Hitachinaka (JP)

(73) Assignee: Hitachi, Ltd., Tokyo (JP)

( * ) Notice: Subject to any disclaimer, the term of this patent is extended or adjusted under 35 U.S.C. 154(b) by 459 days.

(21) Appl. No.: 09/789,567

(22) Filed: Feb. 22, 2001

(65) Prior Publication Data

US 2001/0018219 A1 Aug. 30, 2001

(30) Foreign Application Priority Data

Feb. 28, 2000 (JP) ........................................ 2000-051827

(51) Int. Cl.[7] .............................. G01N 1/34; G01N 1/40
(52) U.S. Cl. ........................... 436/178; 436/94; 436/161
(58) Field of Search .......................... 436/94, 161, 178, 436/180; 422/69, 70, 100; 536/25.4, 25.41

(56) References Cited

U.S. PATENT DOCUMENTS

| 6,379,889 B1 | * | 4/2002 | Apffel et al. ................... 435/6 |
| 2002/0094565 A1 | * | 7/2002 | Sakurai et al. ........... 435/285.3 |
| 2002/0123043 A1 | * | 9/2002 | Hutchens et al. .............. 435/6 |

FOREIGN PATENT DOCUMENTS

| JP | 2-289596 | 11/1990 |
| JP | 8-320274 | 12/1996 |
| JP | 11-266864 | 10/1999 |

* cited by examiner

*Primary Examiner*—Jan M. Ludlow
(74) *Attorney, Agent, or Firm*—Mattingly, Stanger & Malur, P.C.

(57) ABSTRACT

The present invention absorbs and captures nucleic components from various specimens by a single stationary phase and finally recovers the nucleic components by eluting the captured nucleic components from the stationary phase. This invention enables recovery of nucleic components without reducing the concentrations of nucleic acids and detection of specific nucleic components such as specific viruses.

11 Claims, 4 Drawing Sheets

METHOD OF RECOVERING A PLURALITY OF NUCLEIC ACIDS BY AN IDENTICAL STATIONARY PHASE AND AN APPARATUS THEREOF

BACKGROUND OF THE INVENTION

The present invention relates to a method of recovering nucleic acids and an apparatus thereof, more particularly a method and apparatus fit to recover nucleic acids from some kinds of sample substances without reducing the concentrations of the nucleic acids.

As the molecular biology advances, many kinds of gene-related technologies have been developed and used to isolate and identify various infected genes. As the result, these molecular biological techniques have been employed by a wide variety of fields including medical, diagnostic, and testing fields, enabling various new diagnostic methods that had not been realized by conventional methods and dramatically shortening test periods.

This rapid progress is attributed mainly by a nucleic acid amplifying method, particularly by PCR (Polymerase Chain Reaction).

As PCR can peculiarly amplify nucleic segments of a specific structure in a solution, for example, PCR can be used to testify to the existence of an extremely small amount of viruses in blood indirectly by amplifying and detecting a nucleic acid which is the gene of the virus.

However, PCR has some problems when it is used for daily testing jobs in a clinical field. The main concern is extraction and refining of nucleic acids in preprocessing. These steps are greatly affected by the inhibiting factors which remain unremoved after refining. Hemoglobin in blood and surface-active agent used for extraction have been widely known as such inhibiting factors.

Further, the extraction process requires time- and labor-consuming complicated manual operations by experts, which mainly causes a hospital to hesitate to employ a new gene testing system. The automation of this process has been longed for.

In a blood center which must quickly detect HCVs (hepatitis C virus), HIV (human immunodeficiency virus), and so on in a great many blood specimens, a screening (sieving) method is sometimes employed to quicken the test. The screening method comprises steps of mixing some specimens into one and testing it. This is because such viruses (HCV, HIV, etc.) are rarely detected and most specimen mixtures are free from such viruses. Only when such viruses are detected in a specimen mixture, the specimens of the specimen mixture are individually tested.

However, in this screening method, the specimen mixture is diluted too much for example, one fiftieth when 50 specimens are combined into one or one five-hundredth when ten 50-specimen mixtures are combined into one and the concentrations of specimens may go below those required to detect nucleic acids which are the genes of such viruses. In extreme cases, the virus-positive specimens may be evaluated as virus-negative.

For extraction of nucleic acids, Japanese Non-examined Patent Publication H08-320274 (1996) discloses a method of isolating genes by means of a plurality of containers and tips for a single specimen. This method comprises the steps of mounting a first tip onto the pipette nozzle which is moved by a driving mechanism, sucking up a specimen into the first tip, fitting a filter which breaks blood corpuscles to the lower end of the first tip and discharging the specimen from the first tip to a first container through this filter.

The method further comprises the steps of demounting the filter and the first tip from the pipette nozzle, mounting a second tip to the lower end of the second tip, and sucking the specimen from the first container into the second tip.

The method furthermore comprises the steps of fitting a silica membrane filter to the lower end of the second tip to catch genes, and discharging the specimen from the second tip to the second container through the silica membrane filter. With this, genes are caught by the silica membrane and impurities are discharged to the second container.

Further, the method comprises the steps of moving the pipette nozzle to a third container which contains a washing liquid, demounting the silica membrane filter which has genes from the second tip, immersing the filter into the washing liquid in the third container, mounting the third tip to the pipette nozzle from which the second tip was demounted, fitting the washed silica membrane to the lower end of the third tip, sucking up a mixture of the washing liquid and the genes into the third tip, and discharging the mixture to the fourth container.

Japanese Non-examined Patent Publication H02-289596 (1990) discloses a method of using silica particles which can bind with nucleic acids in the presence of a chaotropic agent as a stationary phase for binding nucleic acids. This method comprises the steps of adding a specimen containing nucleic acids to a reaction container which contains a silica particle suspension and guanizithiocyanate buffer solution working as the chaotropic agent, mixing thereof, centrifugally separating a complex which binds nucleic acids to silica particles, and disposing of the supernatant solution.

This method further comprises the steps of adding a washing liquid to the complex residue, washing thereof by means of a vortex mixer, washing the complex precipitate with an aqueous solution of ethanol, washing the precipitate again with acetone, removing acetone, drying the precipitate, adding a buffer solution for elution to the dried complex, and recovering the eluted nucleic acids.

Further, Japanese Non-examined Patent Publication H11-266864 (1999) discloses a method comprising the steps of connecting a nucleic acid capturing tip which contains a silica stationary phase to a nozzle, sucking and discharging a mixture of a specimen which contains nucleic acids and a substance which accelerates the nucleic acids to be bound to the stationary phase, causing the nucleic acids to be bound to the stationary phase in the nucleic acid capturing tip, and washing this tip.

The technology in accordance with Japanese Non-examined Patent Publication H11-266864 (1999) enables automated extraction of nucleic acids.

However, as the technology in accordance with Japanese Non-examined Patent Publication H08-320274 (1996) is so constructed to capture genes when discharging the specimen from the second tip through the silica membrane, the time in which the specimen is in contact with the silica membrane is very short and the rate of capturing genes is low. This may cause a suspected virus-negative case.

Further, the technology in accordance with Japanese Non-examined Patent Publication H02-289596 (1990) requires a centrifugal separation process which is an obstacle to automation of the refining process and takes a lot of time for refining.

As already explained above, although the screening method can increase the test speed, the specimen is diluted down to about one hundredth and high-accuracy detection of viruses (HCV, HIV, etc.) cannot be expected.

Therefore, any other fast and high-precision testing method than the screening method has been longed for.

A comprehensive object of the present invention is to provide a method and apparatus which can automatically recover nucleic segments of a specific structure from a bio specimen.

SUMMARY OF THE INVENTION

The present invention has attained the aforesaid object by Claims, particularly by making a plurality of specimens in contact with a stationary phase for extracting nucleic acids, capturing nucleic acids from the specimens by a single stationary phase, and extracting thereof by an eluate.

A first embodiment of the present invention comprises the steps of making a plurality of specimens containing nucleic components in contact with a stationary phase which can bind with said nucleic components, letting said stationary phase absorb the nucleic acids from the specimens, separating other components which are left unabsorbed from said stationary phase, performing said two processes on each of the other specimens, letting said stationary phase absorb nucleic acids, making an eluate in contact with said stationary phase, discharging thereof, and eluting. This embodiment further comprises the steps of removing components that are not absorbed by the stationary phase, applying a washing liquid to said stationary phase, and discharging the washing liquid to wash the stationary phase.

A second embodiment of the present invention comprises the steps of passing a plurality of specimens containing nucleic components into a capillary having a stationary phase which can bind with said nucleic components, letting said stationary phase absorb and bind with the nucleic acids in the specimen, discharging the other components that are not absorbed and bound by said stationary phase, washing the stationary phase with a washing liquid by sucking the washing liquid into the capillary and discharging the washing liquid into the capillary, repeating said steps on every specimen to cause the identical stationary phase to absorb and bind with the nucleic acids, sucking an eluate into said capillary, discharging the eluate, and thus eluting the nucleic components from the stationary phase. This method can have a step of adding a substance which accelerates binding of the nucleic components having a specific structure with the stationary phase to said specimen before the step of passing a plurality of specimens containing nucleic components into a capillary having a stationary phase which can bind with said nucleic components and letting said stationary phase absorb and bind with the nucleic acids in the specimen. Further, a specimen containing nucleic components can be divided into some samples. Said capillary should have a capillary tip at the end thereof and said stationary phase can be placed in said tip. Further said tip should be mountable on and demountable from said capillary.

A third embodiment of the present invention comprises the steps of preparing a plurality of specimens N (wherein "N" is the number of specimens equal to or greater than 10) containing nucleic components, mixing at least one part of said specimens, preparing mixed specimens N/n (wherein "n" is an integer equal to or greater than 2 and "n" of respective mixed specimens can be identical or different) or a set of mixed specimens and single specimens, making said specimen (mixed or single) in contact with a stationary phase which can bind with said nucleic components, making said stationary phase contact with and absorb the nucleic acids in the specimens, removing the other components which are not absorbed and bound from said stationary phase, feeding a washing liquid to said stationary phase, discharging said washing liquid (thus washing the stationary phase), repeating these steps on each of the other mixed or single specimens, letting the same stationary phase absorb and bind with nucleic components, supplying an eluate to the stationary phase, discharging the eluate from the stationary phase, and thus eluting the nucleic components from said stationary phase. In other words, an object of the present invention is to recover nucleic acids from a lot of specimens or samples without reducing the concentrations of the nucleic acids. If necessary or if circumstances permit, the method in accordance with the present invention can comprise the steps of mixing a plurality of specimens into one sample, performing absorption, binding, and washing steps on this sample (mixture of specimens), repeating these steps on the other mixed or single sample, letting the same stationary phase to absorb nucleic components, and finally eluting nucleic acids from the stationary phase. Further, this method can have a step of adding a substance which accelerates binding of the nucleic components having a specific structure with the stationary phase to said specimen before the step of passing said specimens through the stationary phase. This step can let the stationary phase absorb and bind nucleic acids of the selected structure only.

A fourth embodiment of the present invention comprises the steps of performing a first process which comprises the steps of mixing a plurality of prepared specimens N (wherein "N" is the number of specimens equal to or greater than 10) containing nucleic components, preparing mixed specimens N/n (wherein "n" is an integer equal to or greater than 2 but smaller than "N" and "n" of respective mixed specimens can be identical or different) or a set of mixed specimens and single specimens, making said specimen (mixed or single) in contact with a stationary phase which can bind with nucleic components of a specific structure in a container, and letting said stationary phase absorb and bind with said nucleic acids in the specimen and a second process which comprises a step of removing the other components which are not absorbed and bound from said stationary phase on each of the other mixed or single specimens, letting said stationary phase absorb and bind with the target nucleic acids, supplying an eluate into said container, discharging the eluate from the stationary phase, and thus eluting the nucleic components from said stationary phase.

A fifth embodiment of the present invention comprises the steps of performing a first process which comprises the steps of mixing a plurality of prepared specimens N (wherein "N" is the number of specimens) containing nucleic components, preparing mixed specimens N/n (wherein "n" is an integer equal to or greater than 3 but smaller than "N" and "n" of respective mixed specimens can be identical or different) or a set of mixed specimens and single specimens, making said specimen (mixed or single) in contact with a stationary phase which can bind with nucleic components of a specific structure in a container, and letting said stationary phase absorb and bind with said nucleic acids in the specimen, a second process which comprises a step of removing the other components which are not absorbed and bound from said stationary phase, and a third process which comprises the steps of applying a washing liquid to said stationary phase, discharging said washing liquid, and thus washing said stationary phase on each of the other mixed or single specimens, letting said stationary phase absorb and bind with the target nucleic acids, supplying an eluate into said container, discharging the eluate from the stationary phase, and thus eluting the nucleic components from said stationary phase.

A recovery apparatus which is another embodiment of the present invention comprising the steps of making a specimen containing nucleic components in contact with a stationary phase which can bind with said nucleic components in an area, causing said stationary phase to absorb and bind with said nucleic components, and eluting said nucleic components for recovery comprises a means which scans over said in a preset sequence, a first means which supplies said specimen to said area, a second means which removes the other components which are not absorbed and bound from said stationary phase, and a third process which comprises the steps of applying a washing liquid to said stationary phase, discharging said washing liquid, and thus washing said stationary phase on each of the other mixed or single specimens, a third means which supplies a washing liquid to said area, and a mean which supplies an eluting solution to said stationary phase, wherein said first, second, and third means exert upon each specimen in sequence to cause said stationary phase to absorb and bind with nucleic acids and the eluting solution is supplied to said stationary phase to elute said nucleic acids. Said apparatus can further comprise a means for mixing said specimen with a substance which accelerates nucleic components of a specified structure to be bound to said stationary phase prior to the step of adding said specimen to said stationary phase to contact. Further, said area of said recovery apparatus is a capillary having a capillary tip at the end of the capillary. Said stationary phase can be put in said tip. Furthermore, said tip is mountable on and removable from said capillary.

Another embodiment of the present invention provides a recording medium storing a processing program which executes the steps of applying a specimen containing nucleic components to a stationary phase which can bind with said nucleic components, letting said nucleic components be absorbed and bound by said stationary phase, removing the other components which are left unbound and unabsorbed from said stationary phase, performing these two steps on each of the other specimens, letting nucleic components be absorbed by said stationary phase, supplying an eluting solution to said stationary phase, discharging the used eluting solution, and eluting said nucleic components from said stationary phase. This processing program can contain the steps of applying a washing solution to said stationary phase and removing the used washing solution after a step of removing the other components which are left unbound and unabsorbed from said stationary phase.

By repeating absorption, binding, and washing on the identical stationary phase and finally eluting nucleic components from said stationary phase, the method of the present invention can recover nucleic components without reducing the concentrations of nucleic acids and consequently, this method enables detection of target nucleic acids such as target viruses.

For example, to inspect 50 specimens, said method can mix up all of the specimens or two or more specimens as unit samples (a mixed sample or a set of mixed samples and single samples), perform absorption, binding, washing, and elution on each of the sample unit on a single stationary phase. This method is applicable even when the concentration of nucleic acids of a specimen is very low to be detected. This method can efficiently recover nucleic acids without reducing the concentration of nucleic acids. When a specimen contains an extremely low concentration of a specific nucleic acid to be detected, it is preferable to inspect the specimen alone without mixing it with the others.

DETAILED DESCRIPTION OF THE PREFERRED INVENTION

Some embodiments of the present invention will be explained below with the accompanying drawings.

Figure 1:
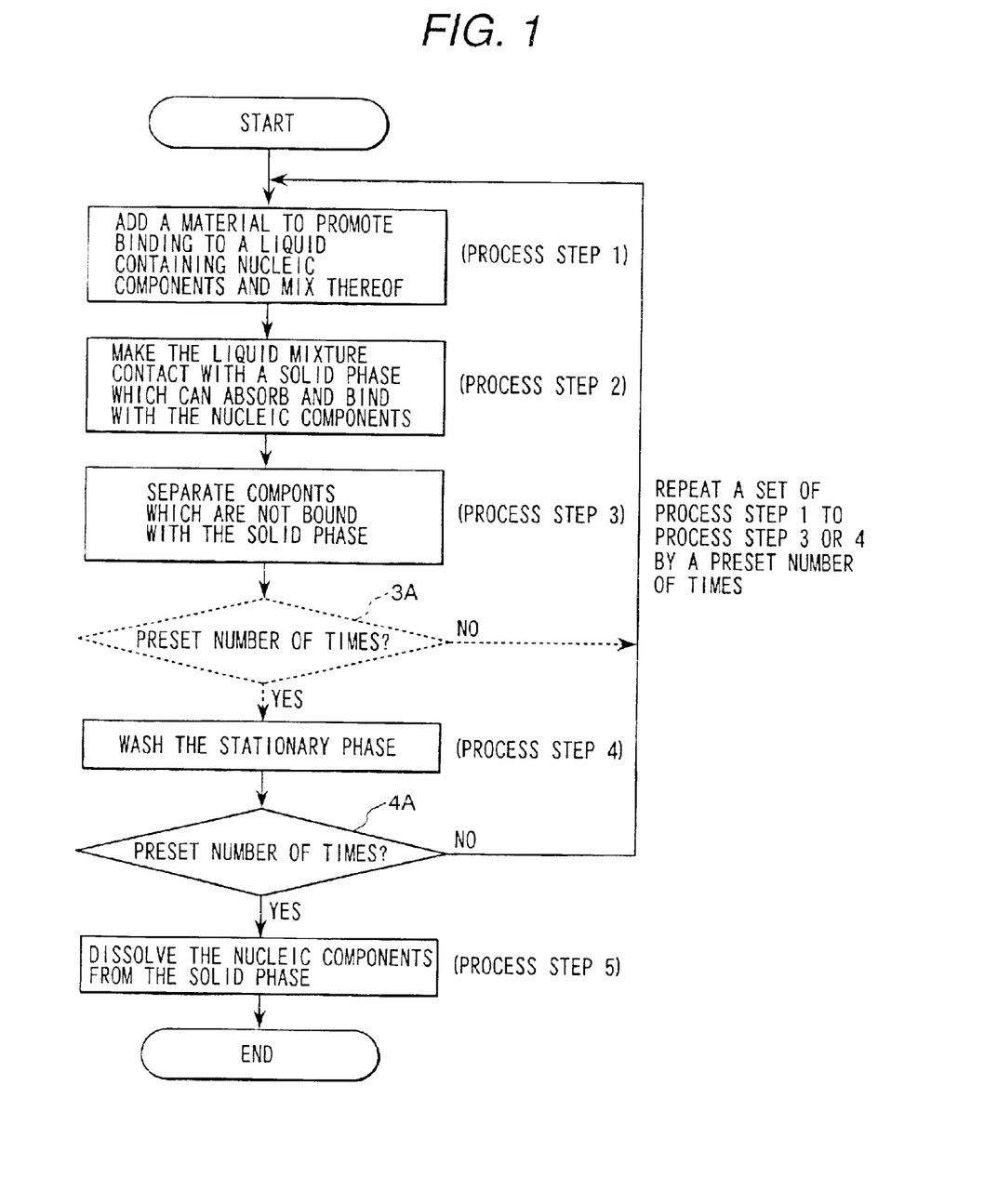
FIG. 1 is a flowchart explaining a method of recovering nucleic acids which is one embodiment of the present invention.
Figure 2:
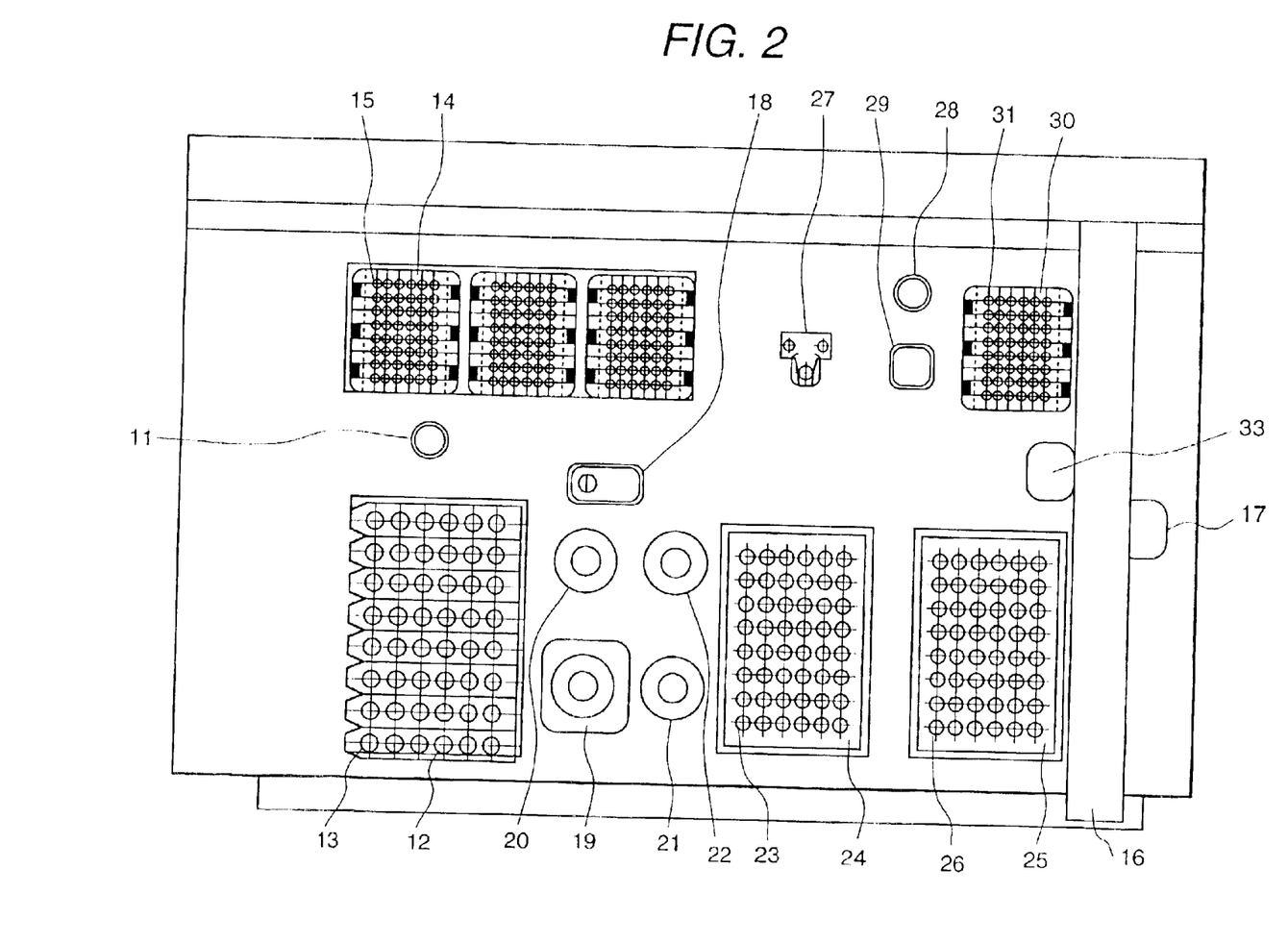
FIG. 2 is a plane view of a nucleic acid recovering apparatus for executing a method of recovering nucleic acids of a specific structure which is one embodiment of the present invention.
Figure 3:
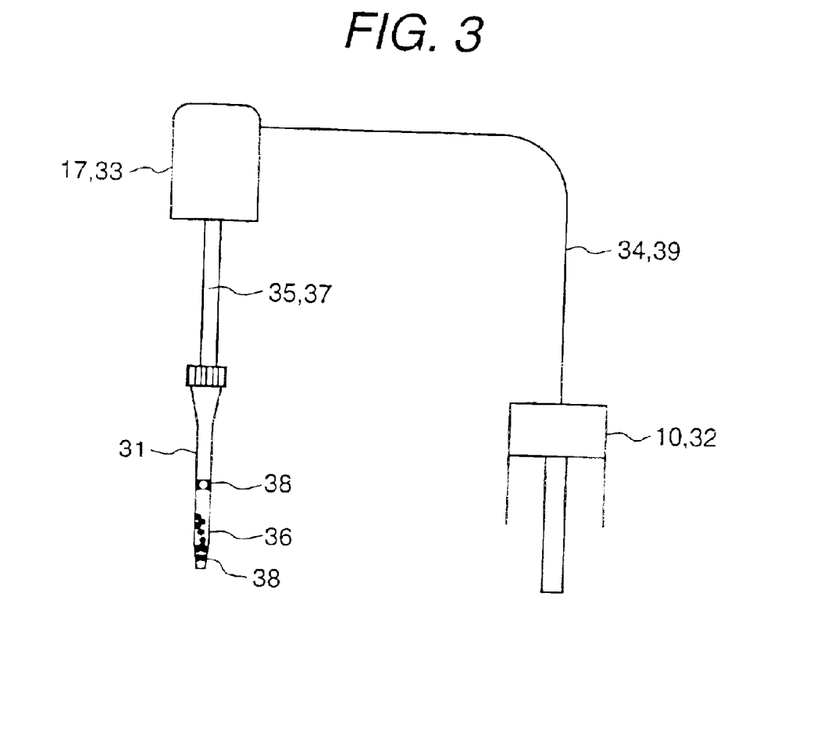
FIG. 3 shows a flow path to recover nucleic components from a syringe through a nozzle holder and a nozzle.

FIG. 1 is a flowchart explaining a method of recovering nucleic acids which is one embodiment of the present invention. FIG. 2 is a plane view of a nucleic acid recovering apparatus for executing a method of recovering nucleic acids of a specific structure which is one embodiment of the present invention. FIG. 3 shows a flow path to recover nucleic components from a syringe through a nozzle holder and a nozzle.

Figure 4:
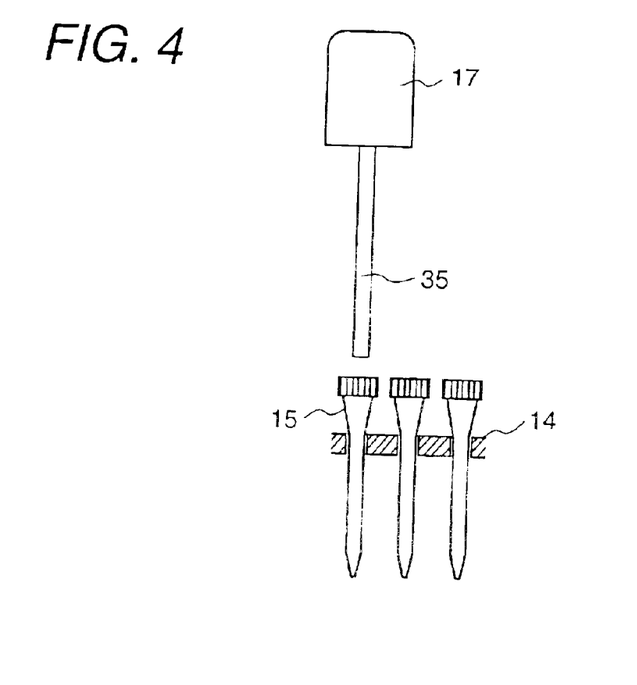
FIG. 4 is an explanatory view of mounting a separation/injection tip to the nozzle.
Figure 5:
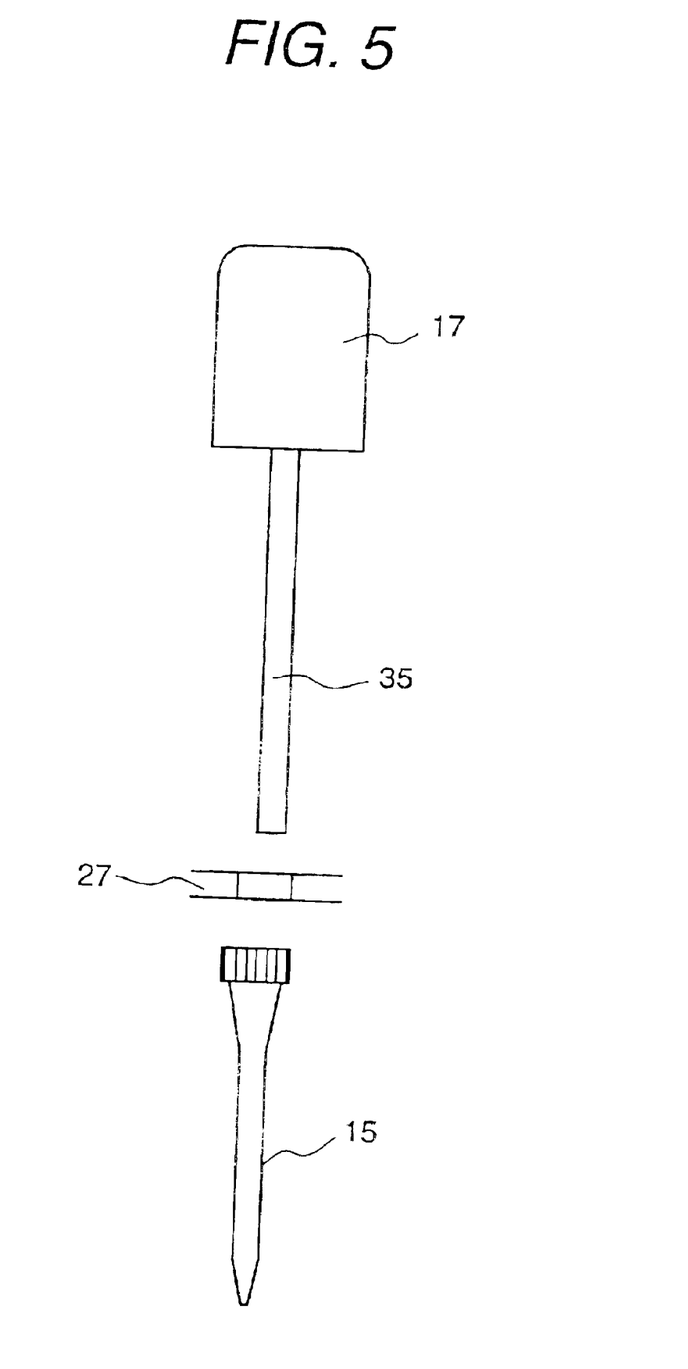
FIG. 5 is an explanatory view of demounting a separation/injection tip from the nozzle.

FIG. 4 is an explanatory view of mounting a separation/injection tip to the nozzle. FIG. 5 is an explanatory view of demounting a separation/injection tip from the nozzle.

The syringes 10 and 32 in FIG. 2 through FIG. 5 can suck and discharge liquid automatically and independently. The syringes 10 and 32 are respectively connected to nozzles 35 and 37 with capillaries 34 and 39.

The nozzles 35 and 37 are respectively held by nozzle holders 17 and 33. The nozzle holders 17 and 33 are mounted on the arm 16 so that they can respectively move in Y and Z directions. The arm 16 is movable in the X direction to cover the major part of the panel of the apparatus. (The "Y" direction is along the shorter edge (up to down) of FIG. 2 and the "X" direction is along the longer edge (left to right) of FIG. 2. The Z direction is perpendicular to FIG. 2.)

The apparatus has three tip holders 14 each of which holds a plurality of tips 15. Any number of tip holders is selectable. The reaction container rack 23 can hold forty-eight reaction containers 24 and the refined material container rack 25 can hold forty-eight refined material containers 26. The refined material container rack 25 has a cooling mechanism (not visible) under it to keep the refined material container rack 25 cooled.

The nucleic acid recovery apparatus has at least one washing liquid bottle 19, one eluting liquid bottle 20, one diluting liquid bottle 21, and one accelerator bottle 22. (The number of bottles is arbitrary.) A heating mechanism (not visible) is provided under the eluting liquid bottle 20 and the accelerator bottle 22 to heat the bottles 19 through 22. The separation tip rack 30 can has forty-eight separation tip (capillary tips) 31.

The nucleic acid recovery apparatus controls the movement of the arm 16 and the nozzle holder 17 to position the arm 16 and the nozzle 35 over the target separation/injection tip 15 in the tip holder 14. The apparatus moves down the nozzle holder 17 to make the nozzle 35 contact with the preset position of the separation/injection tip 15 and automatically mount the tip 15 to the lower end of the nozzle 35. Similarly the nozzle 37, the nozzle holder 33, and the arm 16 are controlled to mount the separation tip 31 to the lower end of the nozzle 37.

Next, the arm 16 and the nozzle holder 17 are controlled to position the nozzle 35 to the upper front of the tip puller 27. Then the nozzle holder 17 is controlled to put the joint between the nozzle 35 and the tip 15 below the tip puller 27, move the nozzle 35 toward the tip puller 27 until the joint fits to the tip puller 27, and move up the nozzle holder 17. With these steps, the tip 15 is automatically pulled out from the nozzle 35. (See FIG. 5.) Similarly, the nozzle 37, the nozzle holder 33, and the arm 16 are controlled to automatically pull out the separation tip 31 from the nozzle 37. It is possible to classify the used tips by types for disposal by providing a plurality of tip pullers by tip types.

The droplet pans 11 and 28 are provided to receive droplets from the nozzles 35 and 37 and drain out the liquid. These pans 11 and 28 also function as the home positions of the nozzles 35 and 37. The washing basin 18 is provided to wash a separation/injection tip 15 mounted on the nozzle 35 of the nozzle holder 17 with water.

Referring to FIG. 3, the separation tip 31 contains two holding material layers 38 and 39 and a stationary phase 36 therebetween in the tip 31. These layers 38 and 39 prevent the stationary phase from moving from the tip 31 into the nozzle 35 or 37 (capillary). The pore size of the holding material 38 is smaller than the outer diameters of stationary phase particles.

To prevent the holding material 38 from going out from the separation tip 31, the separation tip 31 is tapered at the lower end and the outer diameter of the holding material layer 38 is made greater than the inner diameter of the tapered tip end. The separation tip 31 has a projection to guide the holding material 38 to be installed on the inner wall of the tip 31. Further the separation tip 31 can be stored in the separation tip rack 30 of the apparatus (FIG. 2). Specimens are prepared in the rack 12 of the apparatus.

The inspector causes the nucleic acid recovery apparatus to start a preset operation after putting the separation/injection tip rack 14 with separation/injection tips 15, the separation tip rack 30 with the separation tips 31, reagent bottles, reaction containers 24, and the refined material container rack 26 in place on the nucleic acid recovery apparatus. A method of recovering nucleic acids which is an embodiment of the present invention will be explained below referring to FIG. 1 through FIG. 3. This embodiment causes the stationary phase to absorb and bind with every single specimen (instead of mixing the specimens), repeats these steps on every specimen, washes the stationary phase, elutes nucleic components from the stationary phase, and finally recovers a mixture of nucleic components from all specimens. However, as already described, some or all of the specimens can be mixed up and processed in the same manner to get a mixture of nucleic components from all specimens. The present invention is also characterized by collecting all nucleic mixtures onto a single stationary phase site such as a stationary phase placed in a single capillary and eluting the nucleic components from the stationary phase.

The first process comprises the steps of controlling the movement of the arm 16 and the nozzle holder 17 to mount a separation/injection tip 15 onto the nozzle 35, controlling the movement of the arm 16, the nozzle holder 17, and the syringe 10 to suck a preset amount of the binding accelerator from the accelerator bottle 22, causing the nozzle 35 to suck a preset amount of air, moving the tip 15 to the washing basin 18, and wash the outer wall of the tip 15 with clean water.

The first process further comprises the steps of moving the nozzle holder having the washed nozzle to a selected specimen 13, sucking a preset amount of specimen into the nozzle 35 by controlling the operation of the syringe, moving the nozzle holder 17 to a selected reaction container 24 in the reaction container rack 23, and discharging all amount of the specimen from the nozzle.

In this case, it is possible to manually handle specimens instead of placing them on the apparatus. The first process further comprises sucking and discharging the specimen and the binding accelerator into and from the nozzle to mix thereof, moving the nozzle holder 17 to the tip puller 27, and removing the tip 15 from the nozzle 35 by a preset operation.

The second process comprises the steps of controlling the movement of the arm 16 and the nozzle holder 33 to mount a separation tip 31 to the nozzle 37 by a preset operation, moving the nozzle holder 33 to a reaction container 24 having said mixture on the reaction container rack 23, controlling the syringe 32 to suck the mixture into the separation tip 31, further controlling the syringe 32 to repeat suction and discharge into and from the nozzle 37 by a preset number of times, and contacting the mixture with the stationary phase capable of binding with a selected base structure.

The third process comprises the steps of repeating suction and discharge into and from the nozzle 37 by a preset number of times, sucking the mixture from the reaction container 24 into the separation tip 31, controlling the movement of the arm 16 and the nozzle holder 33 to position the nozzle over the drain port 29, discharging the mixture from the separation tip 31 by the control of the syringe 32, then controlling the movement of the arm 16 and the nozzle holder 33 to move the nozzle to the droplet pan 28.

The third-A process judges whether each of the first to third processes is repeated by a preset number of times (that is, as many as the number of specimens). If the repetition is not complete yet, control is returned to the first process using the tip 15 having the same stationary phase 36 (without changing the stationary phase). When the repetition is complete, control is transferred to the fourth process. If this third-A process is provided, the fourth-A process is omitted. Similarly, if this fourth-A process is provided, the third-A process is omitted.

The fourth process comprises the steps of controlling the movement of the arm 16 and the nozzle holder 33 to mount a separation/injection tip 15 to the nozzle 35 by a preset operation, controlling the movement of the arm 16, the nozzle holder 17, and the syringe 10 to suck a preset amount of a washing liquid from the washing liquid bottle 19, moving the nozzle holder 17 to a selected reaction container 24 on the reaction container rack 23, and discharging the washing liquid from the nozzle 35 to the reaction container 24.

The fourth process further comprises the steps of controlling the movement of the arm 16 and the nozzle holder 17 to move the nozzle holder to the tip puller 27 and removing the tip 15 from the nozzle 35 by a preset operation.

The fourth process further comprises the steps of moving the nozzle holder 17, controlling the movement of the arm 16 and the nozzle holder 33 to position the nozzle 35 over a selected reaction container 24 on the reaction container rack, controlling the operation of the syringe 32 to suck a washing liquid into the separation tip 31, repeating suction and discharge by the preset number of times by controlling the operation of the syringe 32 to wash the stationary phase 36 with the washing liquid. It is also possible to feed the mixture from the reaction container 24 directly into the nozzle 37 or the separation/injection tip 15 through another capillary (instead of sucking the mixture).

After suction and discharge is repeated by a preset number of times, the fourth process further comprises the steps of sucking a washing liquid from a reaction container 24 into the separation tip 31, controlling the movement of the arm 16 and the nozzle holder 33 to move the nozzle to the drain port 29, discharging the washing liquid from the separation tip 31 by the operation of the syringe 32, and controlling the arm 16 and the nozzle holder 33 to move the nozzle to the droplet pan 28.

The fourth process can be repeated by a preset number of times if necessary. For repetition of the process at higher efficiency, the process can comprise the steps of sucking a washing liquid by a number of times into the tip 15, discharging a required quantity of the liquid to the reaction container 24, moving the nozzle to the droplet pan 11, operating the separation tip 31, and discharging a required quantity of the washing liquid to the reaction container 24.

The fourth-A process judges whether each of the first to fourth processes is repeated by a preset number of times (that is, as many as the number of specimens). If the repetition is not complete yet, control is returned to the first process using the tip 15 having the same stationary phase 36 (without changing the stationary phase). When the repetition is complete, control is transferred to the fifth process.

The fifth process comprises the steps of controlling the movement of the arm 16 and the nozzle holder 17 to mount a separation/injection tip 15 on the nozzle 35 by a preset operation, controlling the movement of the arm 16, the nozzle holder 17, and the syringe 10 to suck a preset amount of washing liquid from the eluting liquid bottle 20. It is also possible to feed the washing liquid from the bottle 20 directly into the nozzle 37 or the separation/injection tip 15 through another capillary (instead of sucking the liquid). The fifth process further comprises the steps of moving the nozzle holder 17 to the reaction container rack 23 and discharging the washing liquid from the nozzle to a selected reaction container 24.

The fifth process further comprises the steps of controlling the movement of the arm 16 and the nozzle holder 17 until the nozzle holder 17 fits to the tip puller 27, and removing the tip 15 from the nozzle 35 or 37 by a preset operation.

The fifth process further comprises the steps of controlling the movement of the arm 16 and the nozzle holder 17 to position the nozzle over a selected reaction container 24 containing an eluting solution on the reaction container rack 23, controlling the syringe 32 to suck the eluting solution into the separation tip 31, repeating suction and discharge by a preset number of times by the control of the syringe 32, and thus eluting nucleic components from the stationary phase 36.

The fifth process further comprises the steps of sucking the eluting solution from the reaction container 24 into the separation tip 31, controlling the movement of the arm 16 and the nozzle holder 17 to position the nozzle over a selected refined material container on the refined material container rack 25, discharging the eluting solution from the separation tip 31 by the control of the syringe 32, and controlling the movement of the arm, and the nozzle holder 33 to position the nozzle over the droplet pan 28.

The fifth process can be repeated by a preset number of times if necessary. For repetition of the process at higher efficiency, the process can comprise the steps of sucking a washing liquid by a number of times into the tip 15, discharging a required quantity of the liquid to the reaction container 24, moving the nozzle to the droplet pan 11, operating the separation tip 31, and discharging a required quantity of the washing liquid to the reaction container 24.

After completing the fifth process, the apparatus controls the movement of the arm 16 and the nozzle holder 33 until the nozzle fits to the tip puller 27, and demounting the separation tip 31 from the nozzle 37 by a preset operation.

As described above, the first process to the third process or to the fourth process are repeated using an identical tip. During this repetition, the stationary phase 36 in the identical tip accumulates nucleic components of all specimens. Finally, the fifth process is performed on this stationary phase. This method can recover nucleic components without reducing the concentrations of nucleic acids and enables detection of nucleic acids of specific viruses in the nucleic acids.

In other words, for inspection of fifty specimens, the first process to the third process or to the fourth process are repeated on each of the specimens using an identical tip (without diluting the specimens). This method can efficiently recover nucleic acids even from specimens containing nucleic acids whose concentration is not enough to be detected without reducing the concentrations. Further, this method uses a stationary phase 36 to capture nucleic acids and enables automatic recovery of nucleic acids. This method further comprises a sixth process which keeps cooling the liquid for eluting nucleic components of a selected structure (eluted in the fifth process).

As described above, the embodiment of the present invention can provide a quick, simple, accurate and inexpensive method and apparatus for automatically recovering nucleic components of a specific structure from biological specimens containing nucleic acids without reducing the concentration of the specimens.

Particularly, this method is effective for quick treatment of a lot of large-quantity specimens containing nucleic acids such as blood specimens before blood transfusion. (The conventional nucleic acid recovering method takes much time to treat such a large number of specimens and must classify the specimens into some groups for quick treatment.) The method in accordance with the present invention can quickly recover nucleic acids from a large number of specimens without reducing the concentrations and sensitivity of detection. Naturally, this method can greatly reduce the time to recover nucleic acids from a large quantity of specimens and to detect viruses (such as HCV and HIV) in the specimens.

Further, as this method and apparatus can increase the yield of recovery of nucleic acids from specimens, they are effective when it is doubtful whether nucleic acids whose concentration is very low in a specimen are recovered or when the concentration of a specimen is increased to get a higher yield of recovery of nucleic acids.

In said first process, sodium chloride NaCl can be used as a substance to accelerate nucleic components to be bound with the stationary phase. This accelerator will not give any influence to processes after nucleic components are recovered. This accelerator unlike organic solvents has almost no influence upon human bodies and environments.

The stationary phase capable of binding with nucleic components in the second process can be any as far as it can retain nucleic components in the second process to the fourth process and it is insoluble to the liquids used in the first process to the fourth process. The stationary phase can be prepared by a publicly-known technology and substantially practicable for binding with nucleic acids. Further, this embodiment repeats suction of a solution from a container to a tip and discharging a solution from a tip to a container several times to assure contact between nucleic acids and the stationary phase. This increases the efficiency of binding and reproductivity. Separation of liquid components from the stationary phase in the third process requires no additional process and equipment and can be accomplished by a simple device configuration. The means for washing the stationary phase binding with nucleic components in the fourth process requires no additional process and equipment as well as in the third process and can be accomplished by a simple device configuration. The fourth process can be repeated to assure washing.

The eluting process (the fifth process) comprises suction or injection and discharge of an eluting solution and can be accomplished by a simple device configuration as well as in the second and fourth processes. The fifth process can be repeated several times to increase the yield of recovery. When these processes are performed on each of specimen parts divided from a specimen having nucleic components, the nucleic components accumulated on the stationary phase increases as the specimen parts are sucked. Therefore, even when the concentration of nucleic acids in a specimen is very low, the amount of nucleic acids enough for detection can be obtained by this repetition.

The cooling process as said sixth process cools the solution which passed the fifth process to keep the recovered nucleic acids stable. This process can reduce the evaporation from the recovered liquid.

When a control unit of an automatic analyzing apparatus controls operations so that said first to third or fourth processes may be performed on a plurality of specimens using an identical stationary phase, a processing program must be stored on memory in the control unit. This method is also characterized by medium for recording said processing program.

In other words, said medium must store a processing program which controls the suction, discharging, and movement of said capillary to execute said first to third processes or said first to fourth processes and the fifth process respectively on each of specimens containing nucleic acids using an identical stationary phase.

Said medium can store a processing program which divides one specimen containing nucleic components into a plurality of specimen units and controls the suction, discharging, and movement of said capillary to execute said first to third processes or said first to fourth processes and the fifth process respectively on each of specimen units containing nucleic acids using an identical stationary phase. Therefore, this embodiment of the present invention can provide a method and apparatus for automatically recovering nucleic components having a specific structure from biological specimens.

Embodiment 2

This embodiment prepared a total of ten specimen groups comprising ten mixed specimen groups (4 specimens per mixed specimen group) and ten single specimen groups from fifty biological specimens, performed addition of a binding accelerator, absorption of each specimen group to a stationary phase (silica membrane), removal of materials which are left unabsorbed, washing of the stationary phase on each group, and eluted refined nucleic mixtures containing nucleic acids in all specimens.

What we claim is:

1. A nucleic acid recovering method comprising:
   a process of applying a first specimen containing nucleic acids to a stationary phase and letting said stationary phase bind with said nucleic acids in the specimen,
   a process of removing nucleic acids which are left unbound by said stationary phase,
   a process of performing said applying and removing processes on a second specimen containing nucleic acids and letting said stationary phase bind nucleic acids in said second specimen in addition to said nucleic acids of said first specimen already bound to the stationary phase, and
   a process of applying an eluting solution to said stationary phase, discharging said eluting solution and thereby simultaneously eluting said nucleic acids of both of said first and second specimens from said stationary phase.

2. A nucleic acid recovering method in accordance with claim 1, further comprising a process of applying a washing liquid to said stationary phase and discharging the washing liquid, thus washing the stationary phase after the process of removing nucleic acids which are left unbound by said stationary phase.

3. A nucleic acid recovering method comprising:
   a process of applying a plurality of specimens containing nucleic acids to a stationary phase in a capillary and letting said stationary phase bind with said nucleic acids in one of said specimens,
   a process of removing nucleic acids which are left unbound by said stationary phase,
   a process of applying a washing liquid into said capillary and discharging the washing liquid therefrom to wash the stationary phase,
   a process of repeating the processes of applying specimens, removing components, and applying and discharging a washing liquid, on each of said specimens containing nucleic acids and letting the identical stationary phase bind with said nucleic acids in addition to said nucleic acids of said one of said specimens already bound to said stationary phase, and
   a process of applying an eluting solution into said capillary, discharging said eluting solution therefrom, and thereby simultaneously eluting said nucleic acids of said one of said specimens and of said each of said specimens from said stationary phase in said capillary.

4. A nucleic acid recovering method in accordance with claim 3, further comprising a process of mixing the specimens with a substance which accelerates nucleic acids having a specific structure to be bound to said stationary phase before sucking a specimen into the capillary to contact with said stationary phase.

5. A nucleic acid recovering method in accordance with claim 1, further comprising a first process of dividing a specimen containing nucleic acids into a plurality of samples.

6. A nucleic acid recovering method in accordance with claim 3, wherein said capillary has a capillary tip on its lower end and said stationary phase is placed in said tip.

7. A nucleic acid recovering method in accordance with claim 6, wherein said tip can be mounted on and demounted from said capillary.

8. A nucleic acid recovering method comprising:

a first process of preparing a plurality of specimens N (wherein "N" is the number of specimens) containing nucleic acids, a second process of mixing at least part of said specimens and preparing specimens N/n (wherein "n" is an integer equal to or greater than 2 but smaller than "N", and "n" of respective mixed specimens can be identical or different) or a set of mixed specimens and single specimens, a third process of making one of said specimens (mixed or single) in contact with a stationary phase which can bind with nucleic acids and letting said stationary phase bind with said nucleic acids in the specimen, a fourth process of removing nucleic acids which are not bound from said stationary phase, a fifth process of applying a washing liquid to said stationary phase and discharging said washing liquid, thus washing said stationary phase, a sixth process of repeating said third to fifth processes on each of the other mixed and single specimens containing nucleic acids to bind nucleic acids to said stationary phase in addition to said nucleic acids of said one of said specimens already bound to said stationary phase, and a seventh process of applying an eluting solution to said stationary phase and discharging the eluting solution therefrom, thus simultaneously eluting nucleic acids of said one of said specimens and of said other mixed and single specimens from said stationary phase.

9. A nucleic acid recovering method in accordance with claim 8, further comprising a process of adding a substance which accelerates binding of nucleic acids of a specific structure in said mixed and single specimens with the stationary phase before applying said specimens to said stationary phase for contact.

10. A nucleic acid recovering method comprising:

a first process which comprises the steps of mixing a plurality of prepared specimens N (wherein "N" is the number of specimens and is equal to or greater than 10) containing nucleic acids, preparing mixed specimens N/n (wherein "n" is an integer equal to or greater than 2 but smaller than "N", and "n" of respective mixed specimens can be identical or different) or a set of mixed specimens and single specimens, making one of said specimens (mixed or single) in contact with a stationary phase which can bind with nucleic acids of a specific structure in a container, and letting said stationary phase and bind with said nucleic acids in the specimen, and a second process which comprises a step of removing nucleic acids which are not bound from said stationary phase; wherein said first and second processes are performed on each of the mixed and single specimens containing nucleic acids to and bind target nucleic acids to an identical stationary phase, and wherein an eluting solution is applied to said container and discharged from the container to simultaneously elute nucleic acids of each of said mixed and single specimens from the stationary phase in said container.

11. A nucleic acid recovering method comprising:

a first process which comprises the steps of mixing a plurality of prepared specimens N (wherein "N" is the number of specimens) containing nucleic acids, preparing mixed specimens N/n (wherein "n" is an integer equal to or greater than 3 but smaller than "N", and "n" of respective mixed specimens can be identical or different) or a set of mixed specimens and single specimens, making one of said specimens (mixed or single) in contact with a stationary phase which can bind with nucleic acids of a specific structure in a container, and letting said stationary phase bind with said nucleic acids in the specimen, a second process which comprises a step of removing nucleic acids which are not bound from said stationary phase, a third process which comprises the steps of applying a washing liquid to said stationary phase and discharging said washing liquid, thus washing said stationary phase, and an additional process which comprises the steps of performing said first, second, and third processes on each of the other mixed and single specimens containing nucleic acids to bind target nucleic acids to the stationary phase in addition to said nucleic acids of said one of said specimens already bound to the stationary phase, applying an eluting solution to said container and discharging from the container to simultaneously elute nucleic acids from the stationary phase in said container.

* * * * *